United States Patent
Ikeda

(10) Patent No.: US 9,980,488 B2
(45) Date of Patent: *May 29, 2018

(54) WEED CONTROL COMPOSITION

(71) Applicant: SUMITOMO CHEMICAL COMPANY, LIMITED, Tokyo (JP)

(72) Inventor: Hajime Ikeda, Kasai (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/099,565

(22) Filed: Dec. 6, 2013

(65) Prior Publication Data

US 2015/0157018 A1  Jun. 11, 2015

(51) Int. Cl.
*A01N 43/84* (2006.01)
*A01N 57/20* (2006.01)
*A01N 43/80* (2006.01)

(52) U.S. Cl.
CPC ............ *A01N 43/84* (2013.01); *A01N 43/80* (2013.01); *A01N 57/20* (2013.01)

(58) Field of Classification Search
None
See application file for complete search history.

(56) References Cited

U.S. PATENT DOCUMENTS

2010/0248964 A1 * 9/2010 Yamato ............... A01N 43/58
504/128

FOREIGN PATENT DOCUMENTS

WO  WO 0122814 A1 *  4/2001 ............. A01N 25/04
WO  WO 2013/122241 A1  8/2013

OTHER PUBLICATIONS

Meister et al., "Crop Protection Handbook 2011," vol. 97, Meister Publishing Company, 2011, ISBN: 1-892829-23-1, pp. 6-7 and 424-425 (3 pages total).
Australian Examination Report No. 1 issued in the corresponding Australian Patent Application No. 2013267026 dated Jul. 3, 2017.

* cited by examiner

*Primary Examiner* — Tracy Vivlemore
*Assistant Examiner* — Monica A Shin
(74) *Attorney, Agent, or Firm* — Birch, Stewart, Kolasch & Birch, LLP

(57) ABSTRACT

The present invention relates to a composition comprising crystal of flumioxazin which shows a powder X-Ray diffraction pattern having diffraction peaks with 2θ values)(°) shown in Table 1 of the specification, the pattern being obtained by CuKα rays diffraction analysis, and one or more herbicidal compounds selected from the group B-1, B-2, B-3, B-4, B-5, B-6, B-7, B-8, B-9, B-10, B-11 and B-12 described in the specification. According to the present invention, a wide range of weeds can be controlled in a crop field, land under perennial crops, or non-crop land.

10 Claims, No Drawings

WEED CONTROL COMPOSITION

BACKGROUND OF THE INVENTION

Field of the Invention

The present invention relates to a weed control composition.

Description of the Related Art

Many compounds are known as herbicides in order to control weeds. Also, flumioxazin is known as a herbicide.

PRIOR ART DOCUMENT

Non-Patent Documents

Non-patent Document 1: Crop Protection Handbook, vol. 97 (2011) Meister Publishing Company, ISBN: 1-892829-23-1)

SUMMARY OF THE INVENTION

It is an object of the present invention to provide a weed control composition having high herbicidal effect against weeds.

The inventors of the present invention have made earnest studies to find a weed control composition having high herbicidal effect against weeds and, as a result, found that a composition obtained by combining specified herbicides has high herbicidal effect against weeds. This finding has led to completion of the present invention.

The present invention is as follows.

[1] A composition comprising crystal of flumioxazin which shows a powder X-Ray diffraction pattern having diffraction peaks with 2θ values (°) shown in Table 1, said pattern being obtained by CuKα rays diffraction analysis,

TABLE 1

| 2θ value (°) |
|---|
| 9.8 ± 0.1 |
| 11.4 ± 0.1 |
| 12.7 ± 0.1 |
| 13.8 ± 0.1 |
| 16.0 ± 0.1 |
| 16.4 ± 0.1 |
| 16.7 ± 0.1 | and one or more herbicidal compounds selected from the group B:

Group B:
- B-1. Acetolactic acid synthase inhibitors;
- B-2. Acetyl CoA carboxylase inhibitors;
- B-3. Protoporphyrinogen IX oxidase inhibitors;
- B-4. 4-Hydroxyphenylpyrubic acid dioxygenase inhibitors;
- B-5. Phytoene desaturase inhibitors;
- B-6. Photosystem II inhibitors;
- B-7. Very-long-chain fatty acid synthesis inhibitors;
- B-8. Tubulin synthesis inhibitors;
- B-9. Auxin type herbicides;
- B-10. Enolpyruvylshikimate phosphate synthase inhibitors;
- B-11. Glutamine synthetase inhibitors; and
- B-12. Other herbicides.

[2] The weed control composition according to [1], wherein the compound of the group B is the following compound:

B-1. Acetolactic Acid Synthase Inhibitors:

Pyrithiobac, pyrithiobac-sodium salt, pyriminobac, pyriminobac-methyl, bispyribac, bispyribac sodium salt, pyribenzoxim, pyrimisulfan, pyriftalid, triafamone, amidosulfuron, azimsulfuron, bensulfuron, bensulfuron-methyl, chlorimuron, chlorimuron-ethyl, cyclosulfamuron, ethoxysulfuron, flazasulfuron, flucetosulfuron, flupyrsulfuron, flupyrsulfuron methyl-sodium, foramsulfuron, halosulfuron, halosulfuron-methyl, imazosulfuron, mesosulfuron, mesosulfuron-methyl, metazosulfuron, nicosulfuron, orthosulfamuron, oxasulfuron, primisulfuron, primisulfuron-methyl, propyrisulfuron, pyrazosulfuron, pyrazosulfuron-ethyl, rimsulfuron, sulfometuron, sulfometuron-methyl, sulfosulfuron, trifloxysulfuron-sodium salt, trifloxysulfuron, chlorsulfuron, cinosulfuron, ethametsulfuron, ethametsulfuron-methyl, iodosulfuron, iodosulfuron-methyl-sodium, iofensulfuron, iofensulfuron-sodium, metsulfuron, metsulfuron-methyl, prosulfuron, thifensulfuron, thifensulfuron-methyl, triasulfuron, tribenuron, tribenuron-methyl, triflusulfuron, triflusulfuron-methyl, tritosulfuron, bencarbazone, flucarbazone, flucarbazone-sodium salt, ipfencarbazone, propoxycarbazone, propoxycarbazone-sodium salt, thiencarbazone, thiencarbazone-methyl, cloransulam, cloransulam-methyl, diclosulam, florasulam, flumetsulam, metosulam, penoxsulam, pyroxsulam, imazamethabenz, imazamethabenz-methyl, imazamox, imazamox-ammonium salt, imazapic, imazapic-ammonium salt, imazapyr, imazapyr-isopropylammonium salt, imazaquin, imazaquin-ammoniumsalt, imazethapyr, and imazethapyr-ammonium salt.

B-2. Acetyl CoA Carboxylase Inhibitors:

Clodinafop, clodinafop-propargyl, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, propaquizafop, quizalofop, quizalofop-ethyl, quizalofop-P, quizalofop-P-ethyl, alloxydim, clethodim, sethoxydim, tepraloxydim, tralkoxydim, and pinoxaden.

B-3. Protoporphyrinogen IX Oxidase Inhibitors:

Azafenidin, oxadiazone, oxadiargyl, carfentrazone, carfentrazone-ethyl, saflufenacil, cinidon, cinidon-ethyl, sulfentrazone, pyraclonil, pyraflufen, pyraflufen-ethyl, butafenacil, fluazolate, fluthiacet, fluthiacet-methyl, flufenpyr, flufenpyr-ethyl, flumiclorac, flumiclorac-pentyl, pentoxazone, oxyfluorfen, acifluorfen, aclonifen, chlomethoxynil, chloronitrofen, nitrofen, bifenox, fluoroglycofene, fluoroglycofene-ethyl, fomesafen, fomesafen-sodium salt, lactofen, and compounds represented by the formula (I):

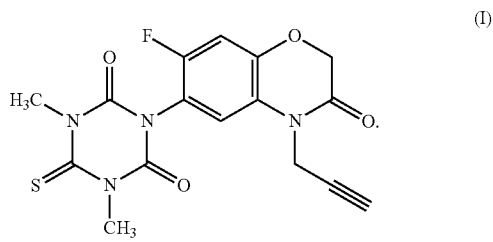 [SMILES: C#CCN1C(=O)COc2cc(F)c(-n3c(=O)n(C)c(=S)n(C)c3=O)cc21]

B-4. 4-Hydroxyphenylpyrubic acid dioxygenase Inhibitors:

Benzobicyclon, bicyclopyrone, mesotrione, sulcotrione, tefuryltrione, tembotrione, isoxachlorotole, isoxaflutole, benzofenap, pyrasulfotole, pyrazolynate, pyrazoxyfen, and topramezone.

B-5. Phytoene Desaturase Inhibitors:

Diflufenican, picolinafen, beflubutamid, norflurazon, fluridone, flurochloridone, and flurtamone.

B-6. Photosystem II Inhibitors:

Ioxynil, ioxynil octanoate, bentazone, pyridate, bromoxynil, bromoxynil octanoate, chlorotoluron, dimefuron, diuron, linuron, fluometuron, isoproturon, isouron, tebuthiuron, benzthiazuron, methabenzthiazuron, propanil, metobromuron, metoxuron, monolinuron, siduron, simazine, atrazine, propazine, cyanazine, ametryne, simetryn, dimethametryn, prometryn, terbumeton, terbuthylazine, terbutryn, trietazine, hexazinone, metamitron, metribuzin, amicarbazone, bromacil, lenacil, terbacil, chloridazon, desmedipham, and phenmedipham.

B-7. Very-long-chain Fatty Acid Synthase Inhibitors:

Propachlor, metazachlor, alachlor, acetochlor, metolachlor, S-metolachlor, butachlor, pretilachlor, thenylchlor, indanofan, cafenstrole, fentrazamide, dimethenamid, dimethenamid-P, mefenacet, pyroxasulfone, fenoxasulfone, naproanilide, anilofos, and flufenacet.

B-8. Tubulin Synthesis Inhibitors:

Trifluralin, pendimethalin, ethafluralin, benfluralin, prodiamine, indaziflam, triaziflam, butamifos, dithiopyr, and thiazopyr.

B-9. Auxin Type Herbicides:

Dicamba and a salt thereof (diglycolamine salt, dimethylammoniumsalt, isopropylammoniumsalt, potassiumsalt, sodium salt, and choline salt), 2,4-D and a salt or ester thereof (butotyl ester, dimethylammonium salt, diolamine salt, ethylhexyl ester, isooctyl ester, isopropylammonium salt, sodium salt, and triisopropanolamine salt), 2,4-DB and a salt or ester thereof (dimethylammonium salt, isooctyl ester, and choline salt), MCPA and a salt or ester thereof (dimethylammonium salt, 2-ethylhexylester, isooctyl ester, sodium salt, and choline salt), MCPB, mecoprop and a salt or ester thereof (dimethylammonium salt, diolamine salt, ethadyl ester, 2-ethylhexyl ester, isooctyl ester, methyl ester, potassiumsalt, sodium salt, tololamine salt, and choline salt), mecoprop-P and a salt or ester thereof (dimethylammonium salt, 2-ethylhexyl ester, isobutyl salt, potassium salt, and choline salt), dichlorprop and a salt or ester thereof (butotyl ester, dimethylammonium salt, 2-ethylhexyl ester, isooctyl ester, methyl ester, potassium salt, sodium salt, and choline salt), dichlorprop-P, dichlorprop-P dimethylammonium, triclopyr and a salt or ester thereof (butotyl esterandtriethylammoniumsalt), fluroxypyr, fluroxypyr-meptyl, picloram and a salt thereof (potassium salt, triisopanolammonium salt, and choline salt), quinclorac, quinmerac, aminopyralid and a salt thereof (potassium salt, triisopanolammonium salt, and choline salt), clopyralid and a salt thereof (olamine salt, potassium salt, triethylammonium salt, and choline salt), and clomeprop.

B-10. Enolpyruvylshikimate Phosphate Synthase Inhibitors:

Glyphosate, glyphosate-isopropylamine salt, glyphosate-trimesium salt, glyphosate-ammonium salt, glyphosate-diammonium salt, glyphosate-sodium salt, glyphosate-potassium salt, and glyphosate-guanidine salt.

B-11. Glutamine Synthetase Inhibitors:

Glufosinate, glufosinate-ammonium salt, glufosinate-P, glufosinate-P-sodium salt, and bialaphos.

B-12. Other Herbicides.

Isoxaben, dichlobenil, methiozolin, diallate, butyrate, triallate, chlorpropham, asulam, phenisopham, benthiocarb, molinate, esprocarb, pyributicarb, prosulfocarb, orbencarb, EPTC, dimepiperate, Swep, aminocyclopyrachlor, aminocyclopyrachlor-methyl, aminocyclopyrachlor-potassium, difenoxuron, methyl dymron, bromobutide, dymron, cumyluron, diflufenzopyr, etobenzanid, tridiphane, amitrole, fenchlorazole, clomazone, maleic hydrazide, oxaziclomefone, cinmethylin, benfuresate, ACN, dalapon, chlorthiamid, flupoxam, bensulide, paraquat, paraquat-dichloride, diquat, and diquat-dibromide.

[3] The weed control composition according to [1], wherein the compound of the group B is a compound selected from a glyphosate isopropylamine salt, a glyphosate-trimesium salt, a glyphosate-ammonium salt, a glyphosate-diammonium salt, a glyphosate-sodium salt, a glyphosate-potassium salt, and a glyphosate-guanidine salt.

[4] The weed control composition according to [1], wherein the compound of the group B is a glufosinate-ammonium salt.

[5] The weed control composition according to [1], wherein the compound of the group B is chlorimuron-ethyl.

[6] The weed control composition according to [1], wherein the compound of the group B is cloransulam-methyl.

[7] The weed control composition according to [1], wherein the compound of the group B is pyroxasulfone.

[8] The weed control composition according to [1], wherein the compound of the group B is a compound selected from dicamba, a dicamba-diglycolamine salt, a dicamba-dimethylammonium salt, a dicamba-isopropylammonium salt, a dicamba-potassium salt, a dicamba-sodium salt, and a dicamba-choline salt.

[9] The weed control composition according to [1], wherein the compound of the group B is a compound selected from a 2,4-D, 2,4-D butotyl ester, a 2,4-D dimethylammonium salt, a 2,4-D diolaminesalt, a 2,4-Dethylhexyl ester, a 2,4-Disooctyl ester, a 2,4-D isopropylammonium salt, a 2,4-D sodium salt, and a 2,4-D triisopropanolammonium salt.

[10] The weed control composition according to [1], wherein the compound of the group B is an imazethapyr-ammonium salt.

[11] The weed control composition according to [1], wherein the compound of the group B is metribuzin.

[12] The weed control composition according to [1], wherein the compound of the group B is isoxaflutole.

[13] The weed control composition according to [1], wherein the compound of the group B is mesotrione.

[14] The weed control composition according to [1], wherein the compound of the group B is tembotrione.

[15] The weed control composition according to [1], wherein the compound of the group B is ametryne.

[16] A method of controlling weeds, the method comprising applying an effective amount of flumioxazin constituted of crystals with crystal forms having diffraction peaks at the angles 2θ (degrees) shown in Table 1 below in a powder X-ray diffraction pattern using Cu—Kα rays and one or more herbicidal compounds selected from the above group B to soil where the weeds are grown or to be grown, or weeds.

[17] The method according to [16], wherein the compound of the group B is the following compound:

B-1. Acetolactic Acid Synthase Inhibitors:

Pyrithiobac, pyrithiobac-sodium salt, pyriminobac, pyriminobac-methyl, bispyribac, bispyribac sodium salt, pyribenzoxim, pyrimisulfan, pyriftalid, triafamone, amidosulfuron, azimsulfuron, bensulfuron, bensulfuron-methyl, chlorimuron, chlorimuron-ethyl, cyclosulfamuron, ethoxysulfuron, flazasulfuron, flucetosulfuron, flupyrsulfuron, flupyrsulfuron methyl-sodium, foramsulfuron, halosulfuron, halosulfuron-methyl, imazosulfuron, mesosulfuron, mesosulfuron-methyl, metazosulfuron, nicosulfuron, orthosulfamuron, oxasulfuron, primisulfuron, primisulfuron-methyl, propyrisulfuron, pyrazosulfuron, pyrazosulfuron-ethyl, rimsulfuron, sulfometuron, sulfometuron-methyl, sulfosulfuron, trifloxysulfuron-sodium salt, trifloxysulfuron, chlorsulfuron, cinosulfuron, ethametsulfuron, ethametsulfuronmethyl, iodosulfuron, iodosulfuron-methyl-sodium, iofensulfuron, iofensulfuron-sodium, metsulfuron, metsulfuron-methyl, prosulfuron, thifensulfuron, thifensulfuronmethyl, triasulfuron, tribenuron, tribenuron-methyl, triflusulfuron, triflusulfuron-methyl, tritosulfuron, bencarbazone, flucarbazone, flucarbazone-sodium salt, ipfencarbazone, propoxycarbazone, propoxycarbazone-sodium salt, thiencarbazone, thiencarbazone-methyl, cloransulam, cloransulam-methyl, diclosulam, florasulam, flumetsulam, metosulam, penoxsulam, pyroxsulam, imazamethabenz, imazamethabenz-methyl, imazamox, imazamox-ammonium salt, imazapic, imazapic-ammonium salt, imazapyr, imazapyr-isopropylammonium salt, imazaquin, imazaquinammoniumsalt, imazethapyr, and imazethapyr-ammonium salt.

B-2. Acetyl CoA Carboxylase Inhibitors:

Clodinafop, clodinafop-propargyl, cyhalofop, cyhalofopbutyl, diclofop, diclofop-methyl, fenoxaprop, fenoxapropethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, propaquizafop, quizalofop, quizalofop-ethyl, quizalofop-P, quizalofop-P-ethyl, alloxydim, clethodim, sethoxydim, tepraloxydim, tralkoxydim, and pinoxaden.

B-3. Protoporphyrinogen IX Oxidase Inhibitors:

Azafenidin, oxadiazon, oxadiargyl, carfentrazone, carfentrazone-ethyl, saflufenacil, cinidon, cinidon-ethyl, sulfentrazone, pyraclonil, pyraflufen, pyraflufen-ethyl, butafenacil, fluazolate, fluthiacet, fluthiacet-methyl, flufenpyr, flufenpyr-ethyl, flumiclorac, flumiclorac-pentyl, pentoxazone, oxyfluorfen, acifluorfen, aclonifen, chlomethoxynil, chloronitrofen, nitrofen, bifenox, fluoroglycofene, fluoroglycofene-ethyl, fomesafen, fomesafen-sodium salt, lactofen, and compounds represented by the formula (I):

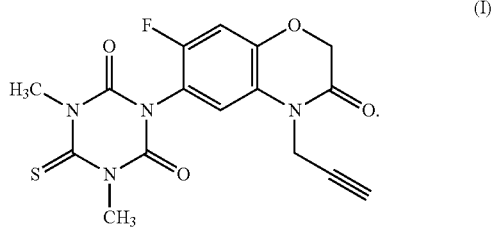 [SMILES: C#CCN1C(=O)COc2cc(F)c(-n3c(=O)n(C)c(=S)n(C)c3=O)cc21]

B-4. 4-Hydroxyphenylpyrubic Acid Dioxygenase Inhibitors:

Benzobicyclon, bicyclopyrone, mesotrione, sulcotrione, tefuryltrione, tembotrione, isoxachlorotole, isoxaflutole, benzofenap, pyrasulfotole, pyrazolynate, pyrazoxyfen, and topramezone.

B-5. Phytoene Desaturase Inhibitors:

Diflufenican, picolinafen, beflubutamid, norflurazon, fluridone, flurochloridone, and flurtamone.

B-6. Photosystem II Inhibitors:

Ioxynil, ioxynil octanoate, bentazone, pyridate, bromoxynil, bromoxynil octanoate, chlorotoluron, dimefuron, diuron, linuron, fluometuron, isoproturon, isouron, tebuthiuron, benzthiazuron, methabenzthiazuron, propanil, metobromuron, metoxuron, monolinuron, siduron, simazine, atrazine, propazine, cyanazine, ametryne, simetryn, dimethametryn, prometryn, terbumeton, terbuthylazine, terbutryn, trietazine, hexazinone, metamitron, metribuzin, amicarbazone, bromacil, lenacil, terbacil, chloridazon, desmedipham, and phenmedipham.

B-7. Very-long-chain Fatty Acid Synthase Inhibitors:

Propachlor, metazachlor, alachlor, acetochlor, metolachlor, S-metolachlor, butachlor, pretilachlor, thenylchlor, indanofan, cafenstrole, fentrazamide, dimethenamid, dimethenamid-P, mefenacet, pyroxasulfone, fenoxasulfone, naproanilide, anilofos, and flufenacet.

B-8. Tubulin Synthesis Inhibitors:

Trifluralin, pendimethalin, ethafluralin, benfluralin, prodiamine, indaziflam, triaziflam, butamifos, dithiopyr, and thiazopyr.

B-9. Auxin Type Herbicides:

Dicamba and a salt thereof (diglycolamine salt, dimethylammoniumsalt, isopropylammoniumsalt, potassiumsalt, sodium salt, and choline salt), 2,4-D and a salt or ester thereof (butotyl ester, dimethylammonium salt, diolamine salt, ethylhexyl ester, isooctyl ester, isopropylammonium salt, sodium salt, and triisopropanolamine salt), 2,4-DB and a salt or ester thereof (dimethylammonium salt, isooctyl ester, and choline salt), MCPA and a salt or ester thereof (dimethylammonium salt, 2-ethylhexylester, isooctyl ester, sodium salt, and choline salt), MCPB, mecoprop and a salt or ester thereof (dimethylammonium salt, diolamine salt, ethadyl ester, 2-ethylhexyl ester, isooctyl ester, methyl ester, potassiumsalt, sodium salt, tololamine salt, and choline salt), mecoprop-P and a salt or ester thereof (dimethylammonium salt, 2-ethylhexyl ester, isobutyl salt, potassium salt, and choline salt), dichlorprop and a salt or ester thereof (butotyl ester, dimethylammonium salt, 2-ethylhexyl ester, isooctyl ester, methyl ester, potassium salt, sodium salt, and choline salt), dichlorprop-P, dichlorprop-P dimethylammonium, triclopyr and a salt or ester thereof (butotyl ester and triethylammonium salt), fluroxypyr, fluroxypyr-meptyl, picloram and a salt thereof (potassium salt, triisopanolammonium salt, and choline salt), quinclorac, quinmerac, aminopyralid and a salt thereof (potassium salt, triisopanolammonium salt, and choline salt), clopyralid and a salt thereof (olamine salt, potassium salt, triethylammonium salt, and choline salt), and clomeprop.

B-10. Enolpyruvylshikimate Phosphate Synthase Inhibitors:

Glyphosate, glyphosate-isopropylamine salt, glyphosate-trimesium salt, glyphosate-ammonium salt, glyphosate-diammonium salt, glyphosate-sodium salt, glyphosate-potassium salt, and glyphosate-guanidine salt.

B-11. Glutamine Synthetase Inhibitors:

Glufosinate, glufosinate-ammonium salt, glufosinate-P, glufosinate-P-sodium salt, and bialaphos.

B-12. Other Herbicides.

Isoxaben, dichlobenil, methiozolin, diallate, butyrate, triallate, chlorpropham, asulam, phenisopham, benthiocarb, molinate, esprocarb, pyributicarb, prosulfocarb, orbencarb, EPTC, dimepiperate, Swep, aminocyclopyrachlor, aminocyclopyrachlor-methyl, aminocyclopyrachlor-potassium, difenoxuron, methyl dymron, bromobutide, dymron, cumyluron, diflufenzopyr, etobenzanid, tridiphane, amitrole, fenchlorazole, clomazone, maleic hydrazide, oxaziclomefone, cinmethylin, benfuresate, ACN, dalapon, chlorthiamid, flupoxam, bensulide, paraquat, paraquat-dichloride, diquat, and diquat-dibromide.

[18] The method according to [16], wherein the compound of the group B is a compound selected from a glyphosate isopropylamine salt, a glyphosate-trimesium salt, a glyphosate-ammonium salt, a glyphosate-diammonium salt, a glyphosate-sodium salt, a glyphosate-potassium salt, and a glyphosate-guanidine salt.

[19] The method according to [16], wherein the compound of the group B is a glufosinate-ammonium salt.

[20] The method according to [16], wherein the compound of the group B is chlorimuron-ethyl.

[21] The method according to [16], wherein the compound of the group B is cloransulam-methyl.

[22] The method according to [16], wherein the compound of the group B is pyroxasulfone.

[23] The method according to [16], wherein the compound of the group B is a compound selected from dicamba, a dicamba-diglycolamine salt, a dicamba-dimethylammonium salt, a dicamba-isopropylammonium salt, a dicamba-potassium salt, a dicamba-sodium salt, and a dicamba-choline salt.

[24] The method according to [16], wherein the compound of the group B is a compound selected from a 2,4-D, 2,4-D butotyl ester, a 2,4-D dimethylammonium salt, a 2,4-D diolamine salt, a 2,4-D ethylhexyl ester, a 2,4-D isooctyl ester, a 2,4-D isopropylammonium salt, a 2,4-D sodium salt, and a 2,4-D triisopropanolammonium salt.

[25] The method according to [16], wherein the compound of the group B is an imazethapyr-ammonium salt.

[26] The method according to [16], wherein the compound of the group B is metribuzin.

[27] The method according to [16], wherein the compound of the group B is isoxaflutole.

[28] The method according to [16], wherein the compound of the group B is mesotrione.

[29] The method according to [16], wherein the compound of the group B is tembotrione.

[30] The method according to [16], wherein the compound of the group B is ametryne.

[31] The method according to any one of [16] to [30], which is a method of controlling weeds in a crop field, land under perennial crops, or non-crop land.

[32] The method according to [31], wherein the crop field is a field for soybean, peanut, corn, cotton, wheat, or sugarcane.

[33] The method according to [31], wherein the land under perennial crops is an orchard.

EFFECT OF THE INVENTION

A wide range of weeds can be controlled by the use of the weed control composition of the present invention.

DETAILED DESCRIPTION OF THE PREFERRED EMBODIMENTS

A weed control composition of the present invention (hereinafter referred to as the composition of the present invention) contains crystal of flumioxazin which shows a powder X-Ray diffraction pattern having diffraction peaks with 2θ values (°) shown in Table 1 above (hereinafter referred to as A-type crystal flumioxazin) and one or more specific herbicidal compounds as effective components.

The A-type crystal flumioxazin used in the composition of the present invention may be prepared by the methods described in Examples and modified methods thereof. A flumioxazin solution or suspension may be used as a starting material to produce the A-type crystal flumioxazin. Also, a solution or suspension of a synthetic reaction crude product containing flumioxazin may be used. A seed crystal may be added in the crystallization and in this case, it is preferable to use a crystal with the crystal form to be prepared. The amount of the seed crystals to be added is preferably 0.0005 parts by weight to 0.02 parts by weight, and more preferably 0.001 parts by weight to 0.01 parts by weight based on 1 part by weight of flumioxazin.

The A-type crystal flumioxazin may be isolated, for example, by filtration, centrifugation, or gradient method. This A-type crystal flumioxazin may be washed with a proper solvent according to the need. Also, the obtained A-type crystal flumioxazin can be improved in purity and quality by recrystallization or slurry purification. Crystals of a solvate may be converted into crystals of a non-solvate by drying with heating under reduced pressure. The degree of dryness of the crystal may be determined by analytical means such as gas chromatography. Also, the polymorph form purity of the crystal may be determined by subjecting the crystal to powder X-ray diffraction measurement to analyze the presence or absence and height of a diffraction peak specific to the solvate crystal. The A-type crystal flumioxazin is a solvate or non-solvate. When a specific hydrophilic organic solvent is used as a solvent for crystallization, there is the case where the A-type crystal flumioxazin forms a solvate. A non-solvate is obtained by drying the solvate with heating under reduced pressure.

In the composition of the present invention, one or more specific herbicidal compounds selected from the group B are used in combination with the A-type crystal flumioxazin.

Group B:
B-1. Acetolactic acid synthase inhibitors;
B-2. Acetyl CoA carboxylase inhibitors;
B-3. Protoporphyrinogen IX oxidase inhibitors;
B-4. 4-Hydroxyphenylpyrubic acid dioxygenase inhibitors;
B-5. Phytoene desaturase inhibitors;
B-6. Photosystem II inhibitors;
B-7. Very-long-chain fatty acid synthase inhibitors;
B-8. Tubulin synthesis inhibitors;
B-9. Auxin type herbicides;
B-10. Enolpyruvylshikimate phosphate synthase inhibitors;
B-11. Glutamine synthetase inhibitors; and
B-12. Other herbicides.

Specific examples of the herbicidal compounds of the group B include the followings:

B-1. Acetolactic Acid Synthase Inhibitors:

Pyrithiobac, pyrithiobac-sodium salt, pyriminobac, pyriminobac-methyl, bispyribac, bispyribac sodium salt, pyribenzoxim, pyrimisulfan, pyriftalid, triafamone, amidosulfuron, azimsulfuron, bensulfuron, bensulfuron-methyl, chlorimuron, chlorimuron-ethyl, cyclosulfamuron, ethoxysulfuron, flazasulfuron, flucetosulfuron, flupyrsulfuron, flupyrsulfuron methyl-sodium, foramsulfuron, halosulfuron, halosulfuron-methyl, imazosulfuron, mesosulfuron, mesosulfuron-methyl, metazosulfuron, nicosulfuron, orthosulfamuron, oxasulfuron, primisulfuron, primisulfuron-methyl, propyrisulfuron, pyrazosulfuron, pyrazosulfuron-ethyl, rimsulfuron, sulfometuron, sulfometuron-methyl, sulfosulfuron, trifloxysulfuron-sodium salt, trifloxysulfuron, chlorsulfuron, cinosulfuron, ethametsulfuron, ethametsulfuron-methyl, iodosulfuron, iodosulfuron-methyl-sodium, iofensulfuron, iofensulfuron-sodium, metsulfuron, metsulfuron-methyl, prosulfuron, thifensulfuron, thifensulfuron-methyl, triasulfuron, tribenuron, tribenuron-methyl, triflusulfuron, triflusulfuron-methyl, tritosulfuron, bencarbazone, flucarbazone, flucarbazone-sodium salt, ipfencarbazone, propoxycarbazone, propoxycarbazone-sodium salt, thiencarbazone, thiencarbazone-methyl, cloransulam, cloransulam-methyl, diclosulam, florasulam, flumetsulam, metosulam, penoxsulam, pyroxsulam, imazamethabenz, imazamethabenz-methyl, imazamox, imazamox-ammonium salt, imazapic, imazapic-ammonium salt, imazapyr, imazapyr-isopropylammonium salt, imazaquin, imazaquin-ammoniumsalt, imazethapyr, and imazethapyr-ammonium salt.

B-2. Acetyl CoA Carboxylase Inhibitors:

Clodinafop, clodinafop-propargyl, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, propaquizafop, quizalofop, quizalofop-ethyl, quizalofop-P, quizalofop-P-ethyl, alloxydim, clethodim, sethoxydim, tepraloxydim, tralkoxydim, and pinoxaden.

B-3. Protoporphyrinogen IX Oxidase Inhibitors:

Azafenidin, oxadiazone, oxadiargyl, carfentrazone, carfentrazone-ethyl, saflufenacil, cinidon, cinidon-ethyl, sulfentrazone, pyraclonil, pyraflufen, pyraflufen-ethyl, butafenacil, fluazolate, fluthiacet, fluthiacet-methyl, flufenpyr, flufenpyr-ethyl, flumiclorac, flumiclorac-pentyl, pentoxazone, oxyfluorfen, acifluorfen, aclonifen, chlomethoxynil, chloronitrofen, nitrofen, bifenox, fluoroglycofene, fluoroglycofene-ethyl, fomesafen, fomesafen-sodium salt, lactofen, and compounds represented by the formula (I):

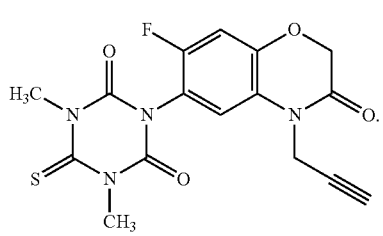

B-4. 4-Hydroxyphenylpyrubic Acid Dioxygenase Inhibitors:

Benzobicyclon, bicyclopyrone, mesotrione, sulcotrione, tefuryltrione, tembotrione, isoxachlorotole, isoxaflutole, benzofenap, pyrasulfotole, pyrazolynate, pyrazoxyfen, and topramezone.

B-5. Phytoene Desaturase Inhibitors:

Diflufenican, picolinafen, beflubutamid, norflurazon, fluridone, flurochloridone, and flurtamone.

B-6. Photosystem II Inhibitors:

Ioxynil, ioxynil octanoate, bentazone, pyridate, bromoxynil, bromoxynil octanoate, chlorotoluron, dimefuron, diuron, linuron, fluometuron, isoproturon, isouron, tebuthiuron, benzthiazuron, methabenzthiazuron, propanil, metobromuron, metoxuron, monolinuron, siduron, simazine, atrazine, propazine, cyanazine, ametryne, simetryn, dimethametryn, prometryn, terbumeton, terbuthylazine, terbutryn, trietazine, hexazinone, metamitron, metribuzin, amicarbazone, bromacil, lenacil, terbacil, chloridazon, desmedipham, and phenmedipham.

B-7. Very-long-chain Fatty Acid Synthase Inhibitors:

Propachlor, metazachlor, alachlor, acetochlor, metolachlor, S-metolachlor, butachlor, pretilachlor, thenylchlor, indanofan, cafenstrole, fentrazamide, dimethenamid, dimethenamid-P, mefenacet, pyroxasulfone, fenoxasulfone, naproanilide, anilofos, and flufenacet.

B-8. Tubulin Synthesis Inhibitors:

Trifluralin, pendimethalin, ethafluralin, benfluralin, prodiamine, indaziflam, triaziflam, butamifos, dithiopyr, and thiazopyr.

B-9. Auxin Type Herbicides:

Dicamba and a salt thereof (diglycolamine salt, dimethylammoniumsalt, isopropylammoniumsalt, potassiumsalt, sodium salt, and choline salt), 2,4-D and a salt or ester thereof (butotyl ester, dimethylammonium salt, diolamine salt, ethylhexyl ester, isooctyl ester, isopropylammonium salt, sodium salt, and triisopropanolamine salt), 2,4-DB and a salt or ester thereof (dimethylammonium salt, isooctyl ester, and choline salt), MCPA and a salt or ester thereof (dimethylammonium salt, 2-ethylhexylester, isooctyl ester, sodium salt, and choline salt), MCPB, mecoprop and a salt or ester thereof (dimethylammonium salt, diolamine salt, ethadyl ester, 2-ethylhexyl ester, isooctyl ester, methyl ester, potassium salt, sodium salt, tololamine salt, and choline salt), mecoprop-P and a salt or ester thereof (dimethylammonium salt, 2-ethylhexyl ester, isobutyl salt, potassium salt, and choline salt), dichlorprop and a salt or ester thereof (butotyl ester, dimethylammonium salt, 2-ethylhexyl ester, isooctyl ester, methyl ester, potassium salt, sodium salt, and choline salt), dichlorprop-P, dichlorprop-P dimethylammonium, triclopyr and a salt or ester thereof (butotyl esterandtriethylammoniumsalt), fluroxypyr, fluroxypyrmeptyl, picloram and a salt thereof (potassium salt, triisopanolammonium salt, and choline salt), quinclorac, quinmerac, aminopyralid and a salt thereof (potassium salt, triisopanolammonium salt, and choline salt), clopyralid and a salt thereof (olamine salt, potassium salt, triethylammonium salt, and choline salt), and clomeprop.

B-10. Enolpyruvylshikimate Phosphate Synthase Inhibitors:

Glyphosate, glyphosate-isopropylamine salt, glyphosate-trimesium salt, glyphosate-ammonium salt, glyphosate-diammonium salt, glyphosate-sodium salt, glyphosate-potassium salt, and glyphosate-guanidine salt.

B-11. Glutamine Synthetase Inhibitors:

Glufosinate, glufosinate-ammonium salt, glufosinate-P, glufosinate-P-sodium salt, and bialaphos.

B-12. Other Herbicides.

Isoxaben, dichlobenil, methiozolin, diallate, butyrate, triallate, chlorpropham, asulam, phenisopham, benthiocarb, molinate, esprocarb, pyributicarb, prosulfocarb, orbencarb, EPTC, dimepiperate, Swep, aminocyclopyrachlor, aminocyclopyrachlor-methyl, aminocyclopyrachlor-potassium, difenoxuron, methyl dymron, bromobutide, dymron, cumyluron, diflufenzopyr, etobenzanid, tridiphane, amitrole, fenchlorazole, clomazone, maleic hydrazide, oxaziclomefone, cinmethylin, benfuresate, ACN, dalapon, chlorthiamid, flupoxam, bensulide, paraquat, paraquat-dichloride, diquat, and diquat-dibromide.

The compounds given as examples of the compound of the group B are compounds described in Non-patent Documents 1 and 2 and Patent Documents 3 to 5, and may be produced by publicly known production methods, and/or are commercially available as preparations containing the compounds.

In the composition of the present invention, as the compound to be combined with the A-type crystal flumioxazin and selected from the group B, particularly, a glyphosate-isopropylamine salt, a glyphosate-trimesium salt, a glyphosate-ammonium salt, a glyphosate-diammonium salt, a glyphosate-sodium salt, a glyphosate-potassium salt, a glyphosate-guanidine salt, a glufosinate-ammonium salt, chlorimuron-ethyl, cloransulam-methyl, pyroxasulfone, an imazethapyr-ammonium salt, metribuzin, 2,4-D, a 2,4-D butotyl ester, a 2,4-D dimethylammonium salt, a 2,4-D diolamine salt, a 2,4-D ethylhexyl ester, a 2,4-D isooctyl ester, a 2,4-D isopropylammonium salt, a 2,4-D sodium salt, a 2,4-D triisopropanolamine salt, dicamba, a dicamba-diglycolamine salt, a dicamba-dimethylammonium salt, a dicamba-isopropylammonium salt, a dicamba-potassium salt, a dicamba-sodium salt, a dicamba-choline salt, mesotrione, tembotrione, isoxaflutole, and ametryne are preferable.

In the composition of the present invention, a safener may be further added to the combination of the A-type crystal flumioxazin and the compound selected from the group B for use.

Examples of the safener include the following compounds:

Benoxacor, cloquintocet, cloquintocet-mexyl, cyometrinil, cyprosulfamide, dichlormid, dicyclonon, dietholate, fenchlorazole, fenchlorazole-ethyl, fenclorim, flurazole, fluxofenim, furilazole, isoxadifen, isoxadifen-ethyl, mefenpyr, mefenpyr-diethyl, mephenate, naphthalic anhydride, and oxabetrinil.

Those given specifically below are more preferable as the composition of the present invention:

Combination of A-type crystal flumioxazin and glyphosate-isopropylamine salt;

Combination of A-type crystal flumioxazin and glyphosate-trimesium salt;

Combination of A-type crystal flumioxazin and glyphosate-ammonium salt;

Combination of A-type crystal flumioxazin and glyphosate-diammonium salt;

Combination of A-type crystal flumioxazin and glyphosate-sodium salt;

Combination of A-type crystal flumioxazin and glyphosate-potassium salt;

Combination of A-type crystal flumioxazin and glyphosate-guanidine salt;

Combination of A-type crystal flumioxazin and glufosinate-ammonium salt;

Combination of A-type crystal flumioxazin and chlorimuron-ethyl;

Combination of A-type crystal flumioxazin and cloransulam-methyl;

Combination of A-type crystal flumioxazin, chlorimuron-ethyl and pyroxasulfone;

Combination of A-type crystal flumioxazin and pyroxasulfone;

Combination of A-type crystal flumioxazin and imazethapyr-ammonium salt;

Combination of A-type crystal flumioxazin and metribuzin;

Combination of A-type crystal flumioxazin and 2,4-D;

Combination of A-type crystal flumioxazin and 2,4-D butotyl ester;

Combination of A-type crystal flumioxazin and 2,4-D dimethylammonium salt;

Combination of A-type crystal flumioxazin and 2,4-D diolamine salt;

Combination of A-type crystal flumioxazin and 2,4-D ethylhexyl ester;

Combination of A-type crystal flumioxazin and 2,4-D isooctyl ester;

Combination of A-type crystal flumioxazin and 2,4-D isopropylammonium salt;

Combination of A-type crystal flumioxazin and 2,4-D sodium salt;

Combination of A-type crystal flumioxazin and 2,4-D triisopropanolamine salt;

Combination of A-type crystal flumioxazin and dicamba;

Combination of A-type crystal flumioxazin and dicamba-diglycolamine salt;

Combination of A-type crystal flumioxazin and dicamba-dimethylammonium salt;

Combination of A-type crystal flumioxazin and dicamba-isopropylammonium salt;

Combination of A-type crystal flumioxazin and dicamba-potassium salt;

Combination of A-type crystal flumioxazin and dicamba-sodium salt;

Combination of A-type crystal flumioxazin and dicamba-choline salt;

Combination of A-type crystal flumioxazin, dicamba, and isoxadifen-ethyl;

Combination of A-type crystal flumioxazin, dicamba-diglycolamine salt, and isoxadifen-ethyl;

Combination of A-type crystal flumioxazin, dicamba-dimethylammonium salt, and isoxadifen-ethyl;

Combination of A-type crystal flumioxazin, dicamba-isopropylammonium salt, and isoxadifen-ethyl;

Combination of A-type crystal flumioxazin, dicamba-potassium salt, and isoxadifen-ethyl;

Combination of A-type crystal flumioxazin, dicamba-sodium salt, and isoxadifen-ethyl;

Combination of A-type crystal flumioxazin, dicamba-choline salt, and isoxadifen-ethyl;

Combination of A-type crystal flumioxazin and mesotrione;

Combination of A-type crystal flumioxazin and tembotrione;

Combination of A-type crystal flumioxazin and isoxaflutole;

Combination of A-type crystal flumioxazin and ametryne;

Combination of A-type crystal flumioxazin, isoxaflutole, and cyprosulfamide;

Combination of A-type crystal flumioxazin, tembotrione, and isoxadifen;

Combination of A-type crystal flumioxazin and saflufenacil;

Combination of A-type crystal flumioxazin, saflufenacil, and glyphosate-isopropylamine salt;

Combination of A-type crystal flumioxazin, saflufenacil, and glyphosate-potassium salt; and Combination of A-type crystal flumioxazin, saflufenacil, and glyphosate-guanidine salt.

The composition of the present invention has herbicidal effect against a wide range of weeds, and can control a wide range of weeds efficiently in a crop field, land under perennial crops, or non-crop land where usual tillage cultivation or non-tillage cultivation is carried out.

Examples of the crop field in the present invention include fields for food crops such as soybean, corn, cotton, wheat, barley, rye, triticale, rice, peanut, common bean, lima bean, azuki bean, cowpeas, mung bean, black lentil, scarlet runner bean, vigna umbellate, moth bean, tepary bean, broad bean, pea, garbanzo bean, lentil, lupine, pigeon pea, and potato; forage crops such as sorghum, oat, and alfalfa; industrial crops such as sugar beet, sunflower, rapeseed, and sugar cane; and garden crops including vegetables. Examples of the vegetables to which the present invention is applied include Solanaceae vegetables (for example, eggplant, tomato, green pepper, bell pepper, and hot pepper); Cucurbitaceae vegetables (for example, cucumber, pumpkin, zucchini, watermelon, and melon); Cruciferous vegetables (for example, Japanese radish, turnip, horse radish, kohlrabi, Chinese cabbage, cabbage, brown mustard, broccoli, and cauliflower); Compositae vegetables (for example, burdock, garland chrysanthemum, artichoke, and lettuce); Liliaceae vegetables (for example, Welsh onion, onion, garlic, asparagus); Umbelliferae vegetables (carrot, parsley, celery, and parsnip); Chenopodiaceae vegetables (for example, spinach and Swiss chard); Labiatae vegetables (for example, Japanese mint, mint, basil, and lavender); strawberry; sweet potato; yam; and aroid.

Also, the crop fields in the present invention include fields for cultivating so-called biomass crops such as *Jatropha curcas*, switchglass, *Miscanthus, Arundo*, reed canarygrass, bluestem, *Erianthus*, napier grass, and *Spartina*, used to produce oil and fats or alcohols for fuels used in heat engines.

The composition of the present invention is particularly applied as a method efficiently controlling weeds in fields for cultivating soybean, peanut, corn, cotton, wheat, or sugarcane among the above crop fields.

When the composition of the present invention is applied to a field for sugarcane, stem fragments cut so as to have one stalk may be used as the stem fragment of sugar cane, or stem fragments having a size of 2 cm to 15 cm may be used in the cultivation of sugar cane. Sugar cane cultivation methods using such stem fragments are publicly known (WO09/000398, WO09/000399, WO09/000400, WO09/000401, and WO09/000402) and carried out under the brand name of Plene (trademark).

Examples of the land under perennial crops in the present invention include orchards, tea gardens, mulberry gardens, coffee plantations, banana gardens, coconut gardens, flower/tree gardens, flower/tree fields, seeding fields, breeding farms, woodlands, and garden parks. Examples of fruit trees in the present invention include kernel fruits (for example, apples, European pears, Japanese pears, Chinese quince, and Quinces), stone fruits (for example, peaches, plums, nectarines, Japanese apricots, cherries, apricots, and prunes), citruses (*Citrus unshiu*, oranges, lemons, limes, and grapefruits), nut trees (for example, Japanese chest nuts, walnuts, hazel nuts, almonds, pistachios, cashew nuts, and macadamia nuts), berry fruits (for example, blueberries, cranberries, blackberries, and raspberries), grapes, permissions, olives, and loquats.

The composition of the present invention is applied as a method for efficiently controlling weeds, particularly, in orchards among the above lands under perennial crops.

Examples of the non-crop lands in the present invention include playgrounds, vacant lands, railroad sides, parks, car parks, roadsides, river beds, areas under power cables, housing sites, and sites for factories.

In the present invention, any type of crop may be used as the crops cultivated in crop field without any particular limitation insofar as it is a variety usually cultivated as crops.

This variety of plants includes plants to which resistance to protoporphyrinogen IX oxidase inhibitors such as flumioxazin; 4-hydroxyphenylpyrubic acid dioxygenase inhibitors such as isoxaflutole; acetolactic acid synthase inhibitors such as imazethapyr and thifensulfuron-methyl; acetyl-CoA carboxylase inhibitors such as sethoxydim; 5-enolpyruvyl-shikimate-3-phosphoric acid synthase inhibitors such as glyphosate; glutamine synthetase inhibitors such as glufosinate; auxin type herbicides such as 2,4-D and dicamba; and herbicides such as bromoxinyl are imparted by classical breeding methods or genetic modification technologies.

As examples of crops to which resistance has been imparted by classical breeding methods, corn resistant to imidazolinone type acetolactic acid synthase inhibitory herbicides such as imazethapyr is given and has already been commercially available under the trade name of Clearfield (trademark). Examples of such crops include STS soybeans resistant to sulfonylurea type acetolactic acid synthase inhibitory herbicides such as thifensulfuron-methyl. Similarly, examples of a plant to which resistance to an acetyl CoA carboxylase inhibitor such as trione oxime-based or aryloxyphenoxypropionic acid-based herbicide has been imparted by classical breeding methods include SR corn.

Examples of a plant to which resistance has been imparted by genetic modification technologies include corn, soybeans and cotton resistant to glyphosate, and they have already been commercially available under the trade names of RoundupReady (registered trade mark), Agrisure (registered trademark) GT, Gly-Tol (registered trademark) and the like. Similarly, there are corn, soybeans and cotton resistant to glufosinate by genetic modification technologies, and they have already been commercially available under the trade names of LibertyLink (registered trademark) and the like. There are varieties of corn and soybeans under the trade names of Optimum (registered trademark) GAT (registered trade mark), which are resistant to both of glyphosate and acetolactic acid synthase inhibitors. Similarly, there are soybeans resistant to imidazolinone type acetolactic acid synthase inhibitors by genetic modification technologies, and they have been developed under the name of Cultivance. Similarly, there is cotton resistant tobromoxynil by genetic modification technologies, and this has already been commercially available under the trade name of BXN (registered trademark). Similarly, there is a variety of soybean sold under the trade name of RoundupReady (registered trademark) 2 Xtend as a soybean resistant to both of glyphosate and dicamba by genetic modification technologies. Similarly, there has been developed cotton resistant to both of glyphosate and dicamba by genetic modification technologies.

A gene encoding aryloxyalkanoate dioxygenase may be introduced to produce a crop which becomes resistant to phenoxy acid type herbicides such as 2,4-D, MCPA, dichlorprop and mecoprop, and aryloxyphenoxypropionic acid type herbicides such as quizalofop, haloxyfop, fluazifop, diclofop, fenoxaprop, metamifop, cyhalofop and clodinafop (Wright et al. 2010: Proceedings of National Academy of Science. 107 (47): 20240-20245). Cultivars of soybean and cotton, which show the resistance to 2,4-D, have been developed under the brand of Enlist.

A gene encoding a 4-hydroxyphenyl pyruvic acid dioxygenase (hereinafter referred to as HPPD) inhibitor, the gene having resistance to HPPD, may be introduced to create a plant resistant to a HPPD inhibitor (US2004/0058427). A gene capable of synthesizing homogentisic acid which is a product of HPPD in a separate metabolic pathway even if HPPD is inhibited by a HPPD inhibitor is introduced, with the result that a plant having resistance to the HPPD inhibitor can be created (WO02/036787). A gene expressing excess HPPD may be introduced to produce HPPD in such an amount as not to adversely affect the growth of plants even in the presence of a HPPD inhibitor, with the result that a plant having resistance to the HPPD inhibitor can be created (WO96/38567). Besides introduction of the gene expressing excess HPPD, a gene encoding prephenate dehydrogenase is introduced in order to increase the yield of p-hydroxyphenyl pyruvic acid which is a substrate of HPPD to create a plant having resistance to the HPPD inhibitor (Rippert P et. al., 2004 Engineering plant shikimate pathway for production of tocotrienol and improving herbicide resistance. Plant Physiol. 134: 92-100).

Examples of a method of producing crops resistant to herbicides include, other than the above, the gene introducing methods described in WO98/20144, WO2002/46387, and US2005/0246800.

The above crops include, for example, crops which can synthesize selective toxins and the like known as the genus *Bacillus* by using genetic modification technologies.

Examples of the toxins developed in such genetically modified plants include insecticidal proteins derived from *Bacillus cereus* and *Bacillus popilliae*; δ-endotoxins such as Cry1Ab, Cry1Ac, Cry1F, Cry1Fa2, Cry2Ab, Cry3A, Cry3Bb1, Cry9C, Cry34, and Cry35ab derived from *Bacillus thuringiensis*; insecticidal proteins such as VIP1, VIP2, VIP3, and VIP3A; insecticidal proteins derived from nematodes; toxins produced by animals such as scorpion toxins, spider toxins, bee toxins, and neurotoxins specific to insects; filamentous fungus toxins; plant lectins; agglutinin; trypsin inhibitors, serine protease inhibitors, and protease inhibitors such as patatin, cystatin, and papain inhibitors; ribosome inactivating proteins (RIP) such as lysine, corn-RIP, abrin, lufin, saporin, and bryodin; steroid metabolic enzymes such as 3-hydroxysteroid oxidase, ecdysteroid-UDP-glucosyltransferase, and cholesterol oxidase; ecdysone inhibitors; HMG-CoA reductase; ion channel inhibitors such as sodium channel and calcium channel inhibitors; juvenile hormone esterase; diuretic hormone receptors; stilbene synthase; bibenzyl synthase; chitinase; and glucanase.

The toxins expressed in these transgenic plants include hybrid toxins, partially deficient toxins and modified toxins, which derive from δ-endotoxin proteins such as Cry1Ab, Cry1Ac, Cry1F, Cry1Fa2, Cry2Ab, Cry3A, Cry3Bb1, Cry9C, Cry34Ab and Cry35Ab, and insecticidal proteins such as VIP1, VIP2, VIP3 and VIP3A. The hybrid toxins are created by new combinations of domains having different proteins by using genetic modification technologies. As the partially defective toxins, Cry1Ab in which part of the amino acid sequences is missing is known. In the modified toxin, one or more of amino acids of a natural type toxin is replaced. Examples of these toxins and genetically modified plants capable of synthesizing these toxins are described in, for example, EP-A-0374753, WO93/07278, WO95/34656, EP-A-0427529, EP-A-451878, and WO 03/052073. Resistance to noxious insects belonging to order Coleoptera, order Diptera, and order Lepidoptera is imparted to plants by toxins contained in these genetically modified plants.

Also, genetically modified plants which contain one or more insecticidal genes resistant to harmful insects and develop one or more toxins have been already known and some of these plants have been put on the market. Examples of these genetically modified plants include YieldGard (registered trademark) (corn variety expressing Cry1Ab toxin), YieldGard Rootworm (registered trademark) (corn variety expressing Cry3Bb1 toxin), YieldGard Plus (registered trademark) (corn variety expressing Cry1Ab and Cry3Bb1 toxins), Herculex I (registered trademark) (corn variety expressing phosphinothricin N-acetyltransferase (PAT) for imparting resistance to a Cry1Fa2 toxin and glufosinate), NatureGard (registered trademark), AGRISURE (registered trademark) CB Advantage (Bt11 corn borer (CB) trait), Protecta (registered trademark); and the like.

Also, genetically modified cotton which contains one or more insecticidal genes resistant to harmful insects and develops one or more toxins has been already known and some of cotton have been put on the market. Examples of these genetically modified cotton include BollGard (registered trademark) (cotton variety expressing Cry1Ac toxin), BollGard (registered trademark) II (cotton variety expressing Cry1Ac and Cry2Ab toxins), BollGard (registered trademark) III (cotton variety expressing Cry1Ac, Cry2Ab and VIP3A toxins), VipCot (registered trademark) (cotton variety expressing VIP3A and Cry1Ab toxins), WideStrike (registered trademark) (cotton variety expressing Cry1Ac and Cry1F toxins) and the like.

Examples of the plant used in the present invention also include plants such as soybeans into which a Rag1 (Resistance Aphid Gene 1) gene is introduced to impart resistance to an aphid.

The plants to be used in the present invention include those provided with resistance to nematodes by using a classical breeding method or genetic modification technologies. Examples of the genetic modification technologies used to provide the resistance to nematodes include RNAi.

The above crops include those to which the ability to produce antipathogenic substances having a selective effect is imparted using genetic modification technologies. For example, PR proteins are known as an example of the antipathogenic substance (PRPs, EP-A-0392225). Such antipathogenic substances and genetically modified plants producing these antipathogenic substances are described in, for example, EP-A-0392225, WO 95/33818, and EP-A-0353191. Examples of the antipathogenic substances developed in such genetically modified plants include ion channel inhibitors such as a sodium channel inhibitor and calcium channel inhibitor (KP1, KP4, and KP6 toxins produced by virus are known); stilbene synthase; bibenzyl synthase; chitinase; glucanase; PR protein; antipathogenic substances produced by microorganisms such as peptide antibiotics, antibiotics having a heteroring, and a protein factor (referred to as a plant disease resistant gene and described in WO 03/000906) relating to plant disease resistance.

The above crops include plants to which useful traits such as an oil component reformation and amino acid-content reinforcing trait are given by genetic modification technologies. Examples of these plants include VISTIVE (trademark) (low linolenic soybean having a reduced linolenic content), high-lysine (high oil) corn (corn having an increased lysine or oil content) and the like.

Moreover, the above crops include stuck varieties obtained by combining two or more useful traits such as the above classical herbicide trait or herbicide resistant gene, gene resistant to insecticidal noxious insects, antipathogenic substance-producing gene, oil component reformation, and amino acid-content reinforcing trait, and allergen reduction trait.

As the weeds which can be controlled by the composition of the present invention, the following examples are given.

Weeds of the family Urticaceae: *Urtica urens;* weeds of the family Polygonaceae: *Polygonum convolvulus, Polygonum lapathifolium, Polygonum pensylvanicum, Polygonum persicaria, Polygonum longisetum, Polygonum aviculare, Polygonum arenastrum, Polygonum cuspidatum, Rumex japonicas, Rumex crispus, Rumex obtusifolius*, and *Rumex acetosa;* weeds of the family Portulacaceae: *Portulaca oleracea;* weeds of the family Caryophyllaceae: *Stellaria media, Cerastium holosteoides, Cerastium glomeratum, Spergula arvensis*, and *Silene gallica;* weeds of the family Molluginaceae: *Mollugo verticillata;* weeds of the family Chenopodiaceae: *Chenopodium album, Chenopodium ambrosioides, Kochia scoparia, Salsola kali*, and *Atriplex* spp.;

weeds of the family Amaranthaceae: *Amaranthus retroflexus, Amaranthus viridis, Amaranthus lividus, Amaranthus spinosus, Amaranthus hybridus, Amaranthus palmeri, Ama-* ranthus rudis, Amaranthus patulus, Amaranthus tuberculatos, Amaranthus blitoides, Amaranthus deflexus, Amaranthus quitensis, Alternanthera philoxeroides, Alternanthera sessilis, and Alternanthera tenella;

weeds of the family Papaveraceae: *Papaver rhoeas* and *Argemone mexicana*;

weeds of the family Brassicaceae: *Raphanus raphanistrum, Raphanus sativus, Sinapis arvensis, Capsella bursa-pastoris, Brassica juncea, Brassica campestris, Descurainia pinnata, Rorippa islandica, Rorippa sylvestris, Thlaspi arvense, Myagrum rugosum, Lepidium virginicum,* and *Coronopus didymus*;

weeds of the family Capparaceae: *Cleome affinis*;

weeds of the family Fabaceae: *Aeschynomene indica, Aeschynomene rudis, Sesbania exaltata, Cassia obtusifolia, Cassia occidentalis, Desmodiumtortuosum, Desmodiumadscendens, Trifolium repens, Pueraria lobata, Vicia angustifolia, Indigofera hirsute, Indigofera truxillensis,* and *Vigna sinensis*;

weeds of the family Oxalidaceae: *Oxalis corniculata, Oxalis strica,* and *Oxalis oxyptera*;

weeds of the family Geraniaceae: *Geranium carolinense* and *Erodium cicutarium*;

weeds of the family Euphorbiaceae: *Euphorbia helioscopia, Euphorbia maculate, Euphorbia humistrata, Euphorbia esula, Euphorbia heterophylla, Euphorbia brasiliensis, Acalypha australis, Croton glandulosus, Croton lobatus, Phyllanthus corcovadensis,* and *Ricinus communis*;

weeds of the family Malvaceae: *Abutilon theophrasti, Sida rhombiforia, Sidacordifolia, Sidaspinosa, Sidaglaziovii, Sida santaremnensis, Hibiscus trionum, Anoda cristata,* and *Malvastrum coromandelianum*;

weeds of the family Sterculiaceae: *Waltheria indica*;

weeds of the family Violaceae: *Viola arvensis,* and *Viola tricolor*;

weeds of the family Cucurbitaceae: *Sicyos angulatus, Echinocystis lobata,* and *Momordica charantia*;

weeds of the family Lythraceae: *Lythrum salicaria*;

weeds of the family Apiaceae: *Hydrocotyle sibthorpioides*;

weeds of the family Sapindaceae: *Cardiospermum halicacabum*;

weeds of the family Primulaceae: *Anagallis arvensis*;

weeds of the family Asclepiadaceae: *Asclepias syriaca* and *Ampelamus albidus*;

weeds of the family Rubiaceae: *Galium aparine, Galium spurium* var. *echinospermon, Spermacoce latifolia, Richardia brasiliensis,* and *Borreria alata*;

weeds of the family Convolvulaceae: *Ipomoea nil, Ipomoea hederacea, Ipomoea purpurea, Ipomoea hederacea* var. *integriuscula, Ipomoea lacunose, Ipomoea triloba, Ipomoea acuminate, Ipomoea hederifolia, Ipomoea coccinea, Ipomoea quamoclit, Ipomoea grandifolia, Ipomoea aristolochiafolia, Ipomoea cairica, Convolvulus arvensis, Calystegia hederacea, Calystegia japonica, Merremia hedeacea, Merremia aegyptia, Merremia cissoids,* and *Jacquemontia tamnifolia*;

weeds of the family Boraginaceae: *Myosotis arvensis*;

weeds of the family Lamiaceae: *Lamium purpureum, Lamium amplexicaule, Leonotis nepetaefolia, Hyptis suaveolens, Hyptis lophanta, Leonurus sibiricus,* and *Stachys arvensis*;

weeds of the family Solanaceae: *Datura stramonium, Solanum nigrum, Solanum americanum, Solanum ptycanthum, Solanum sarrachoides, Solanum rostratum, Solanum aculeatissimum, Solanum sisymbriifolium, Solanum carolinense, Physalis angulata, Physalis subglabrata,* and *Nicandra physaloides*;

weeds of the family Scrophulariaceae: *Veronica hederaefolia, Veronica persica,* and *Veronica arvensis*;

weeds of the family Plantaginaceae: *Plantago asiatica*;

weeds of the family Asteraceae: *Xanthium pensylvanicum, Xanthium occidentale, Helianthus annuus, Matricaria chamomilla, Matricaria perforate, Chrysanthemum segetum, Matricaria matricarioides, Artemisia princeps, Artemisia vulgaris, Artemisia verlotorum, Solidago altissima, Taraxacum officinale, Galinsoga ciliate, Galinsoga parviflora, Senecio vulgaris, Senecio brasiliensis, Senecio grisebachii, Conyza bonariensis, Conyza Canadensis, Ambrosia artemisiaefolia, Ambrosia trifida, Bidens pilosa, Bidens frondosa, Bidens subalternans, Cirsium arvense, Cirsium vulgare, Silybum marianum, Carduus nutans, Lactuca serriola, Sonchus oleraceus, Sonchus asper, Wedelia glauca, Melampodium perfoliatum, Emilia sonchifolia, Tagetes minuta, Blainvillea latifolia, Tridax procumbens, Porophyllum ruderale, Acanthospermum australe, Acanthospermum hispidum, Cardiospermum halicacabum, Ageratum conyzoides, Eupatorium perfoliatum, Eclipta alba, Erechtites hieracifolia, Gamochaeta spicata, Gnaphalium spicatum, Jaegeria hirta, Parthenium hysterophorus, Siegesbeckia orientalis,* and *Soliva sessilis*;

weeds of the family Liliaceae: *Allium canadense* and *Allium vineale*;

weeds of the family Commelinaceae: *Commelina communis, Commelina bengharensis,* and *Commelina erecta*;

weeds of the family Poaceae: *Echinochloa crus-galli, Setaria viridis, Setaria faberi, Setaria glauca, Setaria geniculata, Digitaria ciliaris, Digitaria sanguinalis, Digitaria horizontalis, Digitaria insularis, Eleusine indica, Poa annua, Alospecurus aequalis, Alopecurus myosuroides, Avena fatua, Sorghum halepense, Sorghum vulgare, Agropyron repens, Lolium multiflorum, Lolium perenne, Lolium rigidum, Bromus secalinus, Bromus tectorum, Hordeum jubatum, Aegilops cylindrica, Phalaris arundinacea, Phalaris minor, Apera spica-venti, Panicum dichotomiflorum, Panicum texanum, Panicum maximum, Brachiaria platyphylla, Brachiaria ruziziensis, Brachiaria plantaginea, Brachiaria decumbens, Brachiaria brizantha, Brachiaria humidicola, Cenchrus echinatus, Cenchrus pauciflorus, Eriochloa villosa, Pennisetum setosum, Chloris gayana, Eragrostis pilosa, Rhynchelitrum repens, Dactyloctenium aegyptium, Ischaemum rugosum, Oryza sativa, Paspalum notatum, Paspalum maritimum, Pennisetum clandestinum, Pennisetum setosum,* and *Rottboellia cochinchinensis*;

weeds of the family Cyperaceae: *Cyperus microiria, Cyperus iria, Cyperus odoratus, Cyperus rotundus, Cyperus esculentus,* and *Kyllinga gracillima*; and weeds of the family Equisetaceae: *Equisetum arvense* and *Equisetum palustre*; and the like.

In the composition of the present invention, the mixing ratio by weight of the A-type crystal flumioxazin to the compound selected from the group B is in a range from 1:0.01 to 1:500, preferably 1:0.05 to 1:200, and more preferably 1:0.1 to 1:100.

The composition of the present invention is usually mixed with a solid carrier, liquid carrier, or the like and, according to the need, formulated with surfactants and other preparation aids into preparations such as an emulsion, water-dispersible powder, suspension, and granule. These preparations each contain the A-type crystal flumioxazin and the compound selected from the group B in a total amount of usually 0.1 to 90% by weight and preferably 1 to 80% by weight.

Examples of the solid carrier used for formulating the composition of the present invention include microparticles and granules of compounds such as clays (for example, Kaolinite, diatomaceous earth, synthetic water-containing silicon oxide, Fubasami clay, bentonite, and acid clay), talc, other inorganic minerals (for example, sericite, quartz powder, sulfur powder, activated carbon, and calcium carbonate), and chemical fertilizers (ammonium sulfate, ammonium phosphate, ammonium nitrate, ammonium chloride, andurea), and examples of the liquid carrier include water, alcohols (for example, methanol and ethanol), ketones (for example, acetone, methyl ethyl ketone, and cyclohexanone), aromatic hydrocarbons (for example, toluene, xylene, ethylbenzene, and methylnaphthalene), non-aromatic hydrocarbons (hexane, cyclohexane, and kerosene), esters (for example, ethyl acetate and butyl acetate), nitriles (for example, acetonitrile and isobutyronitrile), ethers (for example, dioxane and diisopropyl ether), acid amides (for example, dimethylformamide and dimethylacetamide), and halogenated hydrocarbons (for example, dichloroethane and trichloroethylene).

Examples of the surfactant used for formulating the composition of the present invention include alkyl sulfates, alkyl sulfonates, alkylaryl sulfonates, alkyl aryl ethers and polyoxyethylene products thereof, polyethylene glycol ethers, polyhydric alcohol esters, and sugar alcohol derivatives. Examples of the other preparation aids include binders and dispersants such as casein, gelatin, polysaccharides (for example, starch, gum arabic, cellulose derivatives, and alginic acid), lignin derivatives, bentonite, synthetic water-soluble polymers (for example, polyvinyl alcohol, polyvinyl pyrrolidone, and polyacrylic acids), and stabilizers such as PAP (acidic isopropyl phosphate), BHT (2,6-tert-butyl-4-methylphenol), BHA (2-/3-tert-butyl-4-methoxyphenol), vegetable oil, mineral oil, fatty acid, and fatty acid ester.

The composition of the present invention is prepared by formulating each component into a preparation by the aforementioned preparation methods, followed by mixing each preparation.

The composition of the present invention formulated into a preparation in this manner may be sprayed on soil or plant body either as it is, or after it is made into a dilute solution by diluting it with water or the like. The composition of the present invention may be further mixed with other herbicides for use, so that an increase in herbicidal effect is expected. Also, the composition of the present invention may be further used together with, for example, insecticides, germicides, plant growth regulators, fertilizers, and soil conditioners.

The amount of the composition to be used is usually 1 to 3000 g in terms of total amount of each compound/ha though this differs depending on the mixing ratio of the A-type crystal flumioxazin to the compound selected from the group B, weather conditions, preparation form, time of use, method of use, place of use, weeds to be controlled, and object crop. When the composition of the present invention is used in the form of emulsion, water-dispersible powder, suspension, or the like, a specified amount of the emulsion, water-dispersible powder, suspension, or the like is usually diluted with 100 to 2000 L/ha for use. Also, when the composition of the present invention is used to perform stem leaves treatment of weeds, adjuvants are added to the dilute solution of the composition of the present invention in order to increase the herbicidal effect against weeds.

Weeds or places where weeds are expected to grow are treated with the composition of the present invention. Examples of the treatment of weeds include treatment of weeds themselves and treatment of soil after weeds grow. The treatment of the place where weeds are expected to grow includes treatment of the surface of soil before weeds grow. Also, examples of the method of controlling weeds according to the present invention include methods in which the A-type crystal flumioxazin and the compound selected from the group B are applied separately to weeds or places where weeds are expected to grow.

The following aspects are given as examples of the method of treatment with the compound of the present invention:

a method in which the compound of the present invention is sprayed on the surface of soil before crops are sowed and before weeds grow;

a method in which the compound of the present invention is sprayed on the surface of soil before crops are sowed and after weeds grow;

a method in which the compound of the present invention is sprayed on weeds before crops are sowed and after the weeds grow;

a method in which the compound of the present invention is sprayed on the surface of soil after crops are sowed but before they germinate, and before weeds grow;

a method in which the compound of the present invention is sprayed on the surface of soil after crops are sowed but before they germinate, and after weeds grow;

a method in which the compound of the present invention is sprayed on weeds after crops are sowed but before they germinate, and after the weeds grow;

a method in which the compound of the present invention is sprayed on the surface of soil in the presence of crops before germination of weeds;

a method in which the compound of the present invention is sprayed on the surface of soil in the presence of crops after weeds grow; and/or a method in which the compound of the present invention is sprayed on the surface of soil in the presence of crops after germination of the weeds.

EXAMPLES

Hereinbelow, the present invention will be described in detail by way of examples, but the present invention is not limited to these examples.

Production Example

Production Examples of A-type crystal flumioxazin used in the method of the present invention will be shown below.

Production Example 1

Flumioxazin (100 mg) was dissolved in methylisobutylketone at 60° C. so as to adjust its concentration to 10.1 mg/mL. The solvent was rapidly cooled to 0° C., followed by being left to stand to obtain A-type crystals.

By X'Pert Pro MPD (manufactured by Nederland PANalytical B.V.), a powder X-ray diffraction pattern of the obtained crystals was measured for each crystal at a scanning range from 2.0° to 40.0° (2θ) using CuKα rays (40 kV, 30 mA).

The pattern of the obtained crystals had the peaks with as 2θ values as shown in Table 2.

TABLE 2

| 2θ value (°) | d value (Å) | Relative intensity (%) |
|---|---|---|
| 9.8 | 9.0179 | 61.1 |
| 11.4 | 7.7556 | 13.1 |
| 12.7 | 6.9645 | 100.0 |
| 13.8 | 6.4117 | 24.1 |
| 16.0 | 5.5347 | 37.9 |
| 16.4 | 5.4006 | 32.4 |
| 16.7 | 5.3042 | 29.1 |

Preparation Examples

Preparation Examples will be shown below. Here, the parts represent parts by weight.

Preparation Example 1

A-type crystal flumioxazin (1 part), a glyphosate-isopropylamine salt (20 parts), polyoxyethylene sorbitan monooleate (3 parts), CMC (carboxymethyl cellulose, the same shall apply hereinbelow) (3 parts), and water (73 parts) are mixed with one another and the mixture is wet-milled to the extent that it has a grain size of 5 micrometer or less to obtain a suspension.

Preparation Example 2

A-type crystal flumioxazin (1 part), a glufosinate-ammoniumsalt (20 parts), polyoxyethylene sorbitan monooleate (3 parts), CMC (3 parts), and water (73 parts) are mixed with one another and the mixture is wet-milled to the extent that it has a grain size of 5 micrometer or less to obtain a suspension.

Preparation Example 3

A-type crystal flumioxazin (0.2 parts), a 2,4-D isopropylamine salt (4 parts), polyoxyethylene sterylphenyl ether (14 parts), calcium dodecylbenzenesulfonate (6 parts), xylene (30 parts), and N,N-dimethylformamide (45.8 parts) are mixed to obtain an emulsion.

Preparation Example 4

A-type crystal flumioxazin (0.2 parts), dicamba-glycolammonium (4 parts), polyoxyethylene sterylphenyl ether (14 parts), calcium dodecylbenzenesulfonate (6 parts), xylene (30 parts), and N,N-dimethylformamide (45.8 parts) are mixed to obtain an emulsion.

Preparation Example 5

A-type crystal flumioxazin (0.5 parts), cloransulam-methyl (0.8 parts), polyoxyethylene sterylphenyl ether (14 parts), calcium dodecylbenzenesulfonate (6 parts), xylene (30 parts), and N,N-dimethylformamide (48.7 parts) are mixed to obtain an emulsion.

Preparation Example 6

A-type crystal flumioxazin (3 parts), pyroxasulfone (4 parts), sodium laurylsulfate (2 parts), synthetic water-containing silicon oxide (91 parts) are thoroughly milled and mixed to obtain a hydrate.

Preparation Example 7

A-type crystal flumioxazin (30 parts), chlorimuron-ethyl (10 parts), sodium laurylsulfate (2 parts), and synthetic water-containing silicon oxide (58 parts) are thoroughly milled and mixed to obtain a hydrate.

Preparation Example 8

A-type crystal flumioxazin (3 parts), chlorimuron-ethyl (1 part), pyroxasulfone (4 parts), sodium lauryl sulfate (2 parts), and synthetic water-containing silicon oxide (90 parts) are thoroughly milled and mixed to obtain a hydrate.

Preparation Example 9

A-type crystal flumioxazin (2 parts), metribuzin (10 parts), sodium laurylsulfate (2 parts), and synthetic water-containing silicon oxide (86 parts) are thoroughly milled and mixed to obtain a hydrate.

Preparation Example 10

A-type crystal flumioxazin (10 parts), isoxaflutole (10 parts), sodium laurylsulfate (2 parts), and synthetic water-containing silicon oxide (78 parts) are thoroughly milled and mixed to obtain a hydrate.

Preparation Example 11

A-type crystal flumioxazin (10 parts), mesotrione (10 parts), sodium laurylsulfate (2 parts), and synthetic water-containing silicon oxide (78 parts) are thoroughly milled and mixed to obtain a hydrate.

Preparation Example 12

A-type crystal flumioxazin (10 parts), tembotrione (10 parts), sodium laurylsulfate (2 parts), and synthetic water-containing silicon oxide (78 parts) are thoroughly milled and mixed to obtain a hydrate.

Preparation Example 13

A-type crystal flumioxazin (2 parts), an imazethapyr-ammoniumsalt (20 parts), polyoxyethylene sorbitan monooleate (3 parts), CMC (3 parts), and water (72 parts) are mixed with one another and the mixture is wet-milled to the extent that it has a grain size of 5 micrometer or less to obtain a suspension.

Preparation Example 14

A-type crystal flumioxazin (1 part), saflufenacil (1 part), a glyphosate-isopropylamine salt (20 parts), polyoxyethylene sorbitan monooleate (3 parts), CMC (3 parts), and water (72 parts) are mixed with one another and the mixture is wet-milled to the extent that it has a grain size of 5 micrometer or less to obtain a suspension.

Test Examples

In Test Examples, the herbicidal effect is evaluated as follows.
[Herbicidal Effect]
In the evaluation of the herbicidal effect, the germination or growth condition of each test weed in a treated area is compared with that in an untreated area and when there is no or almost no difference in germination or growth condition between the treated area and the untreated area at the time of investigation, the case is given "0", and when the test plant perfectly withers and dies, or the germination or growth of the plant is perfectly restricted at the time of investigation, the case is given "100", thereby grading each sample between 0 to 100.

Example 1

Weeds are sowed in a plastic pot filled with soil. A mixture solution of A-type crystal flumioxazin and a glyphosate-isopropylamine salt is uniformly sprayed from above germinated plants three weeks after the weeds are sowed. After the mixture solution is sprayed, soybean, peanut, corn, cotton, or wheat is sowed and the pot is brought in a greenhouse. As a result, high herbicidal effect is found.

Example 2

Weeds are sowed in a plastic pot filled with soil. A mixture solution of A-type crystal flumioxazin and a glyphosate-potassium salt is uniformly sprayed from above germinated plants three weeks after the weeds are sowed. After the mixture solution is sprayed, soybean, peanut, corn, cotton, or wheat is sowed and the pot is brought in a greenhouse. As a result, high herbicidal effect is found.

Example 3

Weeds are sowed in a plastic pot filled with soil. A mixture solution of A-type crystal flumioxazin and a glufosinate-ammonium salt is uniformly sprayed from above germinated plants three weeks after the weeds are sowed. After the mixture solution is sprayed, soybean, peanut, corn, cotton, or wheat is sowed and the pot is brought in a greenhouse. As a result, high herbicidal effect is found.

Example 4

Weeds are sowed in a plastic pot filled with soil. A mixture solution of A-type crystal flumioxazin and a dicamba-glycolamine salt is uniformly sprayed onto the surface of the soil or from above germinated plants on the day when or three weeks after the weeds are sowed. After the mixture solution is sprayed, corn is sowed and the pot is brought in a greenhouse. As a result, high herbicidal effect is found.

Example 5

Weeds are sowed in a plastic pot filled with soil. A mixture solution of A-type crystal flumioxazin and a dicamba-dimethylammonium salt is uniformly sprayed onto the surface of the soil or from above germinated plants on the day when or three weeks after the weeds are sowed. After the mixture solution is sprayed, corn is sowed and the pot is brought in a greenhouse. As a result, high herbicidal effect is found.

Example 6

Weeds are sowed in a plastic pot filled with soil. A mixture solution of A-type crystal flumioxazin and a 2,4-D isopropylamine salt is uniformly sprayed from above germinated plants three weeks after the weeds are sowed. After the mixture solution is sprayed, corn is sowed and the pot is brought in a greenhouse. As a result, high herbicidal effect is found.

Example 7

Soybeans and weeds are sowed in a plastic pot filled with soil. Then, a mixture solution of A-type crystal flumioxazin and chlorimuron-ethyl is uniformly sprayed onto the surface of the soil on the day when the soybeans and weeds are sowed. After the mixture solution is sprayed, the pot is brought in a greenhouse. As a result, high herbicidal effect is found.

Example 8

Soybeans and weeds are sowed in a plastic pot filled with soil. Then, a mixture solution of A-type crystal flumioxazin and cloransulam-methyl is uniformly sprayed onto the surface of the soil on the day when the soybeans and weeds are sowed. After the mixture solution is sprayed, the pot is brought in a greenhouse. As a result, high herbicidal effect is found.

Example 9

Soybeans and weeds are sowed in a plastic pot filled with soil. Then, a mixture solution of A-type crystal flumioxazin and metribuzin is uniformly sprayed onto the surface of the soil on the day when the soybeans and weeds are sowed. After the mixture solution is sprayed, the pot is brought in a greenhouse. As a result, high herbicidal effect is found.

Example 10

Soybeans and weeds are sowed in a plastic pot filled with soil. Then, a mixture solution of A-type crystal flumioxazin and pyroxasulfone is uniformly sprayed onto the surface of the soil on the day when the soybeans and weeds are sowed. After the mixture solution is sprayed, the pot is brought in a greenhouse. As a result, high herbicidal effect is found.

Example 11

Soybeans and weeds are sowed in a plastic pot filled with soil. Then, a mixture solution of A-type crystal flumioxazin, chlorimuron-ethyl and pyroxasulfone is uniformly sprayed onto the surface of the soil on the day when the soybeans and weeds are sowed. After the mixture solution is sprayed, the pot is brought in a greenhouse. As a result, high herbicidal effect is found.

Example 12

Soybeans and weeds are sowed in a plastic pot filled with soil. Then, a mixture solution of A-type crystal flumioxazin and an imazethapyr-ammonium salt is uniformly sprayed onto the surface of the soil on the day when the soybeans and weeds are sowed. After the mixture solution is sprayed, the pot is brought in a greenhouse. As a result, high herbicidal effect is found.

Example 13

Sugarcane and weeds are sowed in a plastic pot filled with soil. Then, a mixture solution of A-type crystal flumioxazin and ametryne is uniformly sprayed onto the surface of the soil on the day when the soybeans and weeds are sowed. After the mixture solution is sprayed, the pot is brought in a greenhouse. As a result, high herbicidal effect is found.

Example 14

Weeds are sowed in a plastic pot filled with soil. Then, a mixture solution of A-type crystal flumioxazin and isoxaflutole is uniformly sprayed onto the surface of the soil on the day when the weeds are sowed. After the mixture solution is sprayed, corn is sowed and the pot is brought in a greenhouse. As a result, high herbicidal effect is found.

Example 15

Weeds are sowed in a plastic pot filled with soil. Then, a mixture solution of A-type crystal flumioxazin and mesotrione is uniformly sprayed onto the surface of the soil on the day when the weeds are sowed. After the mixture solution is sprayed, corn is sowed and the pot is brought in a greenhouse. As a result, high herbicidal effect is found.

Example 16

Weeds are sowed in a plastic pot filled with soil. Then, a mixture solution of A-type crystal flumioxazin and tembotrione is uniformly sprayed onto the surface of the soil on the day when the weeds are sowed. After the mixture solution is sprayed, corn is sowed and the pot is brought in a greenhouse. As a result, high herbicidal effect is found.

Example 17

Weeds are sowed in a plastic pot filled with soil. Then, a mixture solution of A-type crystal flumioxazin, saflufenacil, and a glyphosate-potassium salt is uniformly sprayed on the surface of the soil three weeks after the weeds are sowed. After the mixture solution is sprayed, soybean, peanut, corn, cotton, and wheat are sowed and the pot is brought in a greenhouse. As a result, high herbicidal effect is found.

Example 18

A mixture solution of A-type crystal flumioxazin and a glyphosate-isopropyl salt is uniformly sprayed onto the surface of soil in a pot where grapes, *Citrus unshiu*, peaches, or almonds are cultivated. The plants are grown in the open. As a result, high herbicidal effect is found.

Example 19

A mixture solution of A-type crystal flumioxazin and a glyphosate-potassium salt is uniformly sprayed onto the surface of soil in a pot where grapes, *Citrus unshiu*, peaches, or almonds are cultivated. The plants are grown in the open. As a result, high herbicidal effect is found.

Example 20

A mixture solution of A-type crystal flumioxazin and a glufosinate-ammonium salt is uniformly sprayed onto the surface of soil in a pot where grapes, *Citrus unshiu*, peaches, or almonds are cultivated. The plants are grown in the open. As a result, high herbicidal effect is found.

According to the present invention, a wide range of weeds can be controlled in a crop field, land under perennial crops, or non-crop land.

The invention claimed is:

1. A weed control composition containing active ingredients that consist of:
    (1) crystal of flumioxazin which shows a powder X-Ray diffraction pattern having diffraction peaks with $2\theta$ values(°) shown in Table 1,
    said pattern being obtained by CuKα rays diffraction analysis,

TABLE 1

| $2\theta$ value (°) |
| --- |
| 9.8 ± 0.1 |
| 11.4 ± 0.1 |
| 12.7 ± 0.1 |
| 13.8 ± 0.1 |
| 16.0 ± 0.1 |
| 16.4 ± 0.1 |
| 16.7 ± 0.1 | and
    (2) a herbicidal compound selected from the group B-10:
    Group B-10, Enolpyruvylshikimate phosphate synthase inhibitors,
    wherein a weight ratio of the crystal of flumioxazin to the compound of the group B-10 is 1:10 to 1:100.

2. The weed control composition according to claim 1, wherein the compound of the group B-10 is the following compound:
    B-10, Enolpyruvylshikimate phosphate synthase inhibitors:
    Glyphosate, glyphosate-isopropylamine salt, glyphosate-trimesium salt, glyphosate-ammonium salt, glyphosate-diammonium salt, glyphosate-sodium salt, glyphosate-potassium salt, and glyphosate-guanidine salt.

3. The weed control composition according to claim 1, wherein the compound of the group B-10 is a glyphosate-sodium salt.

4. The weed control composition according to claim 1, wherein the weight ratio of the crystal of flumioxazin to the compound of the group B-10 is 1:20 to 1:100.

5. The weed control composition according to claim 2, wherein the weight ratio of the crystal of flumioxazin to the compound of the group B-10 is 1:20 to 1:100.

6. The weed control composition according to claim 3, wherein the weight ratio of the crystal of flumioxazin to the compound of the group B-10 is 1:20 to 1:100.

7. A method of controlling weeds, the method comprising applying an effective amount of a composition containing active ingredients that consist of:
    (1) crystal of flumioxazin which shows a powder X-Ray diffraction pattern having diffraction peaks with $2\theta$ values(°) shown in Table 1,
    said pattern being obtained by CuKα rays diffraction analysis,

TABLE 1

| $2\theta$ value (°) |
| --- |
| 9.8 ± 0.1 |
| 11.4 ± 0.1 |
| 12.7 ± 0.1 |
| 13.8 ± 0.1 |
| 16.0 ± 0.1 |
| 16.4 ± 0.1 |
| 16.7 ± 0.1 | and (2) a herbicidal compound selected from the group B-10:

Group B-10, Enolpyruvylshikimate phosphate synthase inhibitors, to soil where the weeds are grown or to be grown, or weeds, wherein a weight ratio of the crystal of flumioxazin to the compound of the group B-10 is 1:10 to 1:100.

8. The method according to claim 7, which is a method of controlling weeds in a crop field, land under perennial crops, or non-crop land.

9. The method according to claim 8, wherein the crop field is a field for soybean, peanut, corn, cotton, wheat, or sugarcane.

10. The method according to claim 8, wherein the land under perennial crops is an orchard.

\* \* \* \* \*